(12) United States Patent
Putzig

(10) Patent No.: US 7,754,660 B2
(45) Date of Patent: Jul. 13, 2010

(54) PROCESS TO PREPARE ZIRCONIUM-BASED CROSS-LINKER COMPOSITIONS AND THEIR USE IN OIL FIELD APPLICATIONS

(75) Inventor: Donald Edward Putzig, Newark, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 184 days.

(21) Appl. No.: 12/002,665

(22) Filed: Dec. 18, 2007

(65) Prior Publication Data

US 2009/0151947 A1 Jun. 18, 2009

(51) Int. Cl.
*C01G 25/00* (2006.01)
*C09K 8/60* (2006.01)

(52) U.S. Cl. ............... 507/271; 423/69; 423/81; 423/708; 507/239; 507/267; 562/589

(58) Field of Classification Search ............ 507/271, 507/239, 267; 423/69, 81, 708; 562/589
See application file for complete search history.

(56) References Cited

U.S. PATENT DOCUMENTS

| | | | |
|---|---|---|---|
| 4,460,751 A | | 7/1984 | Hanlon et al. |
| 4,578,488 A | | 3/1986 | Rummo |
| 4,797,216 A | | 1/1989 | Hodge |
| 4,798,902 A | | 1/1989 | Putzig |
| 4,801,389 A | * | 1/1989 | Brannon et al. ............ 507/211 |
| 5,182,408 A | | 1/1993 | Sharif |
| 5,798,320 A | | 8/1998 | Dawson et al. |
| 6,737,386 B1 | | 5/2004 | Moorhouse |
| 2007/0187098 A1 | | 8/2007 | Putzig |
| 2007/0187102 A1 | | 8/2007 | Putzig |
| 2007/0191233 A1 | | 8/2007 | Putzig |

FOREIGN PATENT DOCUMENTS

| | | |
|---|---|---|
| EP | 092755 A1 | 11/1983 |
| EP | 0302544 A | 2/1989 |
| JP | 62198688 | 9/1987 |
| JP | 62250025 | 10/1987 |
| JP | 63022039 | 1/1988 |
| JP | 01108164 | 4/1989 |
| JP | 01260870 | 10/1989 |
| JP | 2006076943 | 3/2006 |

OTHER PUBLICATIONS

Pal et al., Reactions of zirconium(IV) isopropoxide with aliphatic and aromatic hydroxy esters. Part I. Five-, six-, seven- and eight-coordinated zirconium(IV) complexes; Inorganica Chimica Acta (1980), 40(1), 99-103, India. Abstract.

Sharma et al., Synthesis and characterization of heterobimetallic alkoxide triethanolaminate derivatives of zirconium; Synth. React. Inorg. Met.-Org. Chem. (2001), 31(3), 371-379. Pub.: Marcel Dekker, Inc.

Sharma et al., Synthesis and characterization of triethanolaminates of titanium and zirconium; Indian Journal of Chemistry, Section A: Inorganic, Bio-inorganic, Physical, Theoretical & Analytical Chemistry (2001), 40A(6), 568-572. Pub.: National Institute of Science Communication, CSIR, India. Abstract.

* cited by examiner

*Primary Examiner*—Timothy J. Kugel
(74) *Attorney, Agent, or Firm*—Kathryn M. Sanchez

(57) ABSTRACT

A process to prepare a solution of zirconium-alkanolamine-hydroxycarboxylic acid complex is disclosed and use of the solution in oil field applications such as hydraulic fracturing and plugging of permeable zones. The process comprises contacting an alcohol solution of a zirconium complex with an alkanolamine, then with an α-hydroxycarboxylic acid to produce a solution of zirconium-alkanolamine-hydroxycarboxylic acid complex. The solution is particularly suitable for use in a cross-linking composition in hydraulic fracturing and plugging of permeable zones of subterranean formations at temperatures of 275° F. (135° C.) and higher in the formation.

23 Claims, No Drawings

PROCESS TO PREPARE ZIRCONIUM-BASED CROSS-LINKER COMPOSITIONS AND THEIR USE IN OIL FIELD APPLICATIONS

FIELD OF THE INVENTION—SERVER VERSION

The present invention relates to zirconium chelates and their use in oil field applications such as hydraulic fracturing and plugging of permeable zones.

BACKGROUND OF THE INVENTION

The production of oil and natural gas from an underground well (subterranean formation) can be stimulated by a technique called hydraulic fracturing, in which a viscous fluid composition (fracturing fluid) containing a suspended proppant (e.g., sand, bauxite) is introduced into an oil or gas well via a conduit, such as tubing or casing, at a flow rate and a pressure which create, reopen and/or extend a fracture into the oil- or gas-containing formation. The proppant is carried into the fracture by the fluid composition and prevents closure of the formation after pressure is released. Leak-off of the fluid composition into the formation is limited by the fluid viscosity of the composition. Fluid viscosity also permits suspension of the proppant in the composition during the fracturing operation. Cross-linking agents, such as borates, titanates or zirconates, are usually incorporated into the fluid composition to control viscosity.

Typically, less than one third of available oil is extracted from a well after it has been fractured before production rates decrease to a point at which recovery becomes uneconomical. Enhanced recovery of oil from such subterranean formations frequently involves attempting to displace the remaining crude oil with a driving fluid, e.g., gas, water, brine, steam, polymer solution, foam, or micellar solution. Ideally, such techniques (commonly called flooding techniques) provide a bank of oil of substantial depth being driven into a producing well; however, in practice this is frequently not the case. Oil-bearing strata are usually heterogeneous, some parts of them being more permeable than others. As a consequence, channeling frequently occurs, so that the driving fluid flows preferentially through permeable zones depleted of oil (so-called "thief zones") rather than through those parts of the strata which contain sufficient oil to make oil-recovery operations profitable.

Difficulties in oil recovery due to thief zones may be corrected by injecting an aqueous solution of an organic polymer and a cross-linking agent into a subterranean formation under conditions where the polymer will be cross-linked to produce a gel, thus reducing permeability of the subterranean formation to the driving fluid (gas, water, etc.). Polysaccharide-or partially hydrolyzed polyacrylamide-based fluids cross-linked with certain aluminum, titanium, zirconium, and boron based compounds are used in these enhanced oil recovery applications. Cross-linked fluids or gels, whether for fracturing a subterranean formation or for reducing permeability of zones in subterranean formation, are now being used in hotter and deeper wells under a variety of temperature and pH conditions. In these operations the rate of cross-link is critical to the successful generation of viscosity. Frequently the rates of cross-linking with known cross-linking compositions are unacceptable, and new, highly specific compositions are required. Particularly, the need exists for cross-linkers which generate a high, thermally stable viscosity in a high pH environment.

Oil field service companies are currently using zirconium based cross-linkers to generate viscosity in polysaccharide-based fluids useful in hydraulic fracturing, completion and enhanced oil recovery applications. Commercially available, zirconium cross-linkers containing triethanolamine as a chelating ligand cross-link in the desired range and generate and maintain significant viscosity at 250° F. (121° C.), but at higher temperatures greater than or equal to 275° F., 135° C.) cross-link too fast. Replacement of triethanolamine with a hydroxyalkylated ethylenediamine chelating ligand such as in U.S. Pat. No. 4,798,902 gives a complex which cross-links too slowly at 250-275° F. (121-135° C.). The rate of cross-linking is critical to the successful generation of viscosity sufficient to conduct a fracturing operation.

Compositions are known in which aqueous zirconium compounds, triethanolamine and an α-hydroxycarboxylic acid are combined. Various processes have been used in combining these components to produce the compositions, such as those disclosed in U.S. Pat. Nos. 4,460,751; 5,182,408; and 5,798,320.

Some zirconium-based compositions of alkanolamine salts of α-hydroxycarboxylic acid may be used as cross-linkers in mid-high temperature fracturing fluid applications. While it is has been found that such triethanolamine zirconate complexes with α-hydroxycarboxylic acids have slower rates of cross-linking than similar complexes without α-hydroxycarboxylic acids, viscosity generation and retention are sacrificed, especially at temperatures greater than or equal to 275° F. (135° C.).

There is a need for zirconium-based cross-linking compositions which have a desirable 3-8 minute delay in rate of cross-linking without sacrificing the viscosity development capability of the zirconium composition at both lower mid temperature (up to 250° F., 121° C.) and at higher temperature (greater than 250° F., 121° C., especially greater than or equal to 275° F., 135° C.). That is, which will allow the cross-linking compositions to be used at a temperature greater than or equal to 250° F. (121° C.) and maintain adequate viscosity to ensure successful completion of the fracturing operation. The present invention meets these needs.

SUMMARY OF THE INVENTION

The present invention provides a process for preparing a solution of a zirconium complex suitable for use as a cross-linking agent in a fracturing fluid composition comprising: (a) contacting an alcohol solution of a zirconium complex with an alkanolamine at a mole ratio of 2 to 4 moles of alkanolamine per mole of zirconium to form a mixture which is a solvent-based alkanolamine complex of zirconium; (b) contacting the mixture with an α-hydroxycarboxylic acid at a mole ratio of 2 to 4 moles of hydroxycarboxylic acid per mole of zirconium for a period of time sufficient to stabilize the resulting solution of zirconium-alkanolamine-hydroxycarboxylic acid complex. Steps (a) and (b) can be performed at a variety of temperatures, preferably from about 25° C. to about 90° C., more preferably between 50° C. and 80° C.

The present invention further provides a cross-linking composition comprising a solution of a zirconium complex prepared according to the process of this invention and methods to use the composition as a fracturing fluid.

DETAILED DESCRIPTION OF THE INVENTION

Trademarks and tradenames are shown herein in upper case.

This invention provides a process to prepare an effective cross-linking agent for use in cross-linking compositions for oil field applications, which comprises (a) contacting an alcohol solution of a zirconium complex with an alkanolamine at a mole ratio of 2 to 4 moles of alkanolamine per mole of zirconium to form a mixture which is a solvent-based alkanolamine complex of zirconium; (b) contacting the mixture with an α-hydroxycarboxylic acid at a mole ratio of 2 to 4 moles of hydroxycarboxylic acid per mole of zirconium for a period of time sufficient to stabilize the resulting solution of zirconium-alkanolamine-hydroxycarboxylic acid complex.

By "solvent-based" regarding the product of step (a) is meant herein that the primary solvent for the product zirconium complex is alcohol rather than water. The product cross-linking agent ("cross-linker") is a solution of a zirconium complex in an alcohol.

This invention provides compositions which cross-link at a desirable 3-8 minute rate, intermediate between zirconium complexes of hydroxyalkylated ethylenediamine zirconates and triethanolamine zirconates. The cross-linker, which can be used successfully at high pH (about pH 10 and above) and high temperature (greater than or equal to 275° F., 135° C.) conditions, while generating and maintaining a satisfactory viscosity.

The solvent-based alkanolamine complex of zirconium produced in step (a) can be prepared by a process which comprises contacting a solution of a tetraalkyl zirconate in a $C_1$-$C_6$ alcohol with from 2 to 4 moles of an alkanolamine per mole of zirconium. A number of tetraalkyl zirconates (also known as zirconium tetraalkoxides) can be used to prepare the above zirconium complex, e.g., tetra-isopropyl zirconate, tetra-n-propyl zirconate, and tetra-n-butyl zirconate. The preferred tetraalkyl zirconate is tetra-n-propyl zirconate, available as TYZOR NPZ organic zirconate, a solution in n-propanol, with a zirconium content as $ZrO_2$ of about 28% by weight, and available from E. I. du Pont de Nemours and Company, Wilmington, Del.

An alkanolamine is added in an amount of from 2 to 4 moles of an alkanolamine per mole of zirconium. Too little alkanolamine results in an unstable solution and precipitation of solids, which is difficult to handle and difficult to determine amount of an unstable solution to add in fracturing fluid applications. Too much alkanolamine reduces the rate of cross-linking to an undesirably slow rate. Examples of suitable alkanolamines include, but are not limited to, triethanolamine, tri-n-propanolamine, tri-isopropanolamine, diisopropanolamine, and mixtures thereof. Preferably the alkanolamine is triethanolamine.

Contacting the zirconium complex in step (a) with the alkanolamine can be carried out at a variety of temperatures, e.g., between 25° C. and 90° C., preferably between 50° C. and 80° C., and in any order. Preferably this step is carried out under substantially non-aqueous conditions, that is, without the addition of water.

In step (b) an α-hydroxycarboxylic acid is contacted with the mixture produced in step (a), which is a solvent-based zirconium-alkanolamine complex at a ratio of 2 to 4 moles of α-hydroxycarboxylic acid per mole of zirconium. Preferably this ratio is about 3 moles of α-hydroxycarboxylic acid per mole of zirconium. The contacting or reaction step can be carried out at a variety of temperatures, e.g., between 25° C. and 90° C., preferably between 50° C. and 80° C., and in any order. Preferably this step (b) is also carried out under substantially non-aqueous conditions, that is, without the addition of water. However, water may be present, for example as a component in one or more of the zirconium complex in step (a), alkanolamine, alcohol, and/or carboxylic acid.

An α-hydroxycarboxylic acid is added in an amount of from 2 to 4 moles of an α-hydroxycarboxylic acid per mole of zirconium. Too little α-hydroxycarboxylic acid results in an undesirably fast rate of cross-linking. Too much α-hydroxycarboxylic acid results in an unstable solution and precipitation of solids, with the same difficulties as discussed above when too little alkanolamine is added. Examples of suitable α-hydroxycarboxylic acids include, but are not limited to, lactic acid, glycolic acid, malic acid, citric acid, and mixtures thereof. Preferably the α-hydroxycarboxylic acid is lactic acid, glycolic acid, malic acid, or citric acid, more preferably, lactic acid.

Reaction time for step (b) will depend on reaction conditions, such as temperature, pressure, mass transfer rates (e.g., depending on intensity of agitation). Reaction time should be sufficient to stabilize the resulting solution of zirconium-alkanolamine-hydroxycarboxylic acid complex in step (b). By "stabilize" it is meant to indicate that the reaction in step (b) has gone to completion. Typical reaction time at a temperature of 25° C. to 90° C. is 2 to 6 hours.

Optionally a solvent is added to the process in step (a) or in step (b). The solvent may be any aliphatic alcohol having 1 to 6 carbon atoms. Preferably, an aliphatic alcohol is added at a mole ratio of aliphatic alcohol to zirconium of at least 4 to 1 moles of alcohol per mole of zirconium. Preferably the alcohol is methanol, isopropanol, or n-propanol.

The process produces a solution of a zirconium-alkanolamine-hydroxycarboxylic acid complex. This solution is stable, meaning the solution can be stored at ambient temperature for at least six months without precipitation.

The present invention also provides a cross-linking composition which comprises an aqueous liquid; a pH buffer; a cross-linkable organic polymer; and a solution made by a process comprising (a) contacting an alcohol solution of a zirconium complex with an alkanolamine at a mole ratio of 2 to 4 moles of alkanolamine per mole of zirconium to form a mixture which is a solvent-based alkanolamine complex of zirconium; (b) contacting the mixture with an αhydroxycarboxylic acid at a mole ratio of 2 to 4 moles of hydroxycarboxylic acid per mole of zirconium for a period of time sufficient to stabilize the resulting solution of zirconium-alkanolamine-hydroxycarboxylic acid complex.

The aqueous liquid is typically selected from the group consisting of water, aqueous alcohol, and aqueous solution of a clay stabilizer. The alcohol can be the same or different alcohol as the reaction solvent, that is, an alcohol having 1 to 6 carbon atoms. Preferably, when the aqueous liquid is aqueous alcohol, the alcohol is methanol or ethanol. Clay stabilizers include, for example, hydrochloric acid and chloride salts, such as, tetramethylammonium chloride (TMAC) or potassium chloride. Aqueous solutions comprising clay stabilizers may comprise, for example, 0.05 to 0.5 weight % of the stabilizer, based on the combined weight of the aqueous liquid and the organic polymer (i.e., the base gel). Preferably, when the aqueous liquid is an aqueous solution of a clay stabilizer, the clay stabilizer is tetramethylammonium chloride or potassium chloride.

The aqueous liquid can also be a mixture of water and one or more organic solvents. Organic solvents that may be used include alcohols, glycols, polyols, and hydrocarbons such as diesel.

Preferably, the aqueous liquid is water, aqueous methanol, aqueous ethanol, an aqueous solution of potassium chloride, an aqueous solution of tetramethylammonium chloride, or a combination of two or more thereof.

The cross-linking composition comprises an effective amount of a pH buffer to control pH. The pH buffer may be acidic, neutral or basic. The pH buffer is generally capable of controlling the pH from about pH 5 to about pH 12. For example in a composition for use at a pH of 5-7, a fumaric acid-based buffer or a sodium diacetate-based buffer can be used. In a composition for use at a pH of 7-8.5, a sodium bicarbonate-based buffer can be used. In a composition for use at a pH of 9-12, a sodium carbonate or sodium hydroxide-based buffer can be used. Other suitable pH buffers can be used, as are known to those skilled in the art.

The composition further comprises a cross-linkable organic polymer. Suitable cross-linkable organic polymers are selected from the group consisting of solvatable polysaccharides, polyacrylamides and polymethacrylamides. Preferably the organic polymer is a solvatable polysaccharide and is selected from the group consisting of gums, gum derivatives and cellulose derivatives. Gums include guar gum and locust bean gum, as well as other galactomannan and glucomannan gums, such as those derived from sennas, Brazilwood, tera, honey locust, karaya gum and the like. Preferred gum derivatives include hydroxyethylguar (HEG), hydroxypropylguar (HPG), carboxyethylhydroxyethylguar (CEHEG), carboxymethylhydroxypropylguar (CMHPG), and carboxymethyl guar (CMG). Preferred cellulose derivatives include those containing carboxyl groups, such as carboxymethylcellulose (CMC) and carboxymethylhydroxyethylcellulose (CMHEC). The solvatable polysaccharides can be used individually or in combination; usually, however, a single material is used. Guar derivatives and cellulose derivatives are preferred, such as, HPG, CMC and CMHPG. HPG is generally more preferred based upon its commercial availability and desirable properties. However, CMC and CMHPG may be more preferred in cross-linking compositions when the pH of the composition is less than 6.0 or higher than 9.0, or when the permeability of the formation is such that one wishes to keep the residual solids at a low level to prevent damage to the formation. The cross-linkable polymer is normally mixed with the aqueous liquid to form a base gel.

The alcohol solution of zirconium-alkanolamine-hydroxycarboxylic acid complex is the solvent-based alkanolamine complex of zirconium modified with α-hydroxycarboxylic acid, prepared as described previously. Optionally, this may contain an added solvent or solvents, such as an alcohol having 1 to 10 carbon atoms or a polyol such as ethylene glycol.

The cross-linking composition may comprise optional components, including those which are common additives for oil field applications. Thus, the composition may further comprise one or more of proppants, friction reducers, bactericides, hydrocarbons, chemical breakers, polymer stabilizers, surfactants, formation control agents, and the like. Proppants include sand, bauxite, glass beads, nylon pellets, aluminum pellets and similar materials. Friction reducers include polyacrylamides. Hydrocarbons include diesel oil. Chemical breakers break the cross-linked polymer (gel) in a controlled manner and include enzymes, alkali metal persulfate, and ammonium persulfate. Polymer stabilizers include methanol, alkali metal thiosulfate, and ammonium thiosulfate.

These optional components are added in an effective amount sufficient to achieve the desired cross-linking performance based on the individual components, desired cross-linking time, temperature and other conditions present in the formation being fractured or permeable zone being plugged.

The cross-linking composition is produced by mixing the solution of zirconium-alkanolamine-hydroxycarboxylic acid complex with the other components, in any order. For example, in one particular application in an oil field, the solution of zirconium-alkanolamine-hydroxycarboxylic acid complex and optional components are introduced into a formation, while the cross-linkable organic polymer and aqueous liquid are introduced into the formation as a separate stream. The pH buffer is independently admixed with the zirconium solution, the organic polymer and/or the aqueous liquid. Alternatively, all components may be premixed and introduced into a subterranean formation as a single stream. Advantageously, the components may be mixed in different combinations, and more advantageously, the components may be mixed just prior to use to enable easy variation and adjustment of the cross-linking rate.

This invention provides a method for hydraulically fracturing a subterranean formation, which comprises introducing into the formation at a flow rate and pressure sufficient to create, reopen, and/or extend one or more fractures in the formation, a cross-linking composition comprising an aqueous liquid; a pH buffer; a cross-linkable organic polymer, and a zirconate solution made by a process comprising (a) contacting an alcohol solution of a zirconium complex with an alkanolamine at a mole ratio of 2 to 4 moles of alkanolamine per mole of zirconium to form a mixture which is a solvent-based alkanolamine complex of zirconium; (b) contacting the mixture with an αhydroxycarboxylic acid at a mole ratio of 2 to 4 moles of hydroxycarboxylic acid per mole of zirconium for a period of time sufficient to stabilize the resulting solution of zirconium-alkanolamine- hydroxycarboxylic acid complex.

In one embodiment of the method for hydraulically fracturing a subterranean formation, the solution of zirconium-alkanolamine-hydroxycarboxylic acid complex and a base gel are contacted prior to their introduction into the formation, such that the cross-linking agent and polymer react to form a cross-linked gel. In this method, the base gel is prepared by mixing the cross-linkable organic polymer with the aqueous liquid. The cross-linked gel composition is prepared by mixing the base gel with a solution of zirconium cross-linking agent, made by a process comprising (a) contacting an alcohol solution of a zirconium complex with an alkanolamine at a mole ratio of 2 to 4 moles of alkanolamine per mole of zirconium to form a mixture which is a solvent-based alkanolamine complex of zirconium; (b) contacting the mixture with an α-hydroxycarboxylic acid at a mole ratio of 2 to 4 moles of hydroxycarboxylic acid per mole of zirconium for a period of time sufficient to stabilize the resulting solution of zirconium-alkanolamine-hydroxycarboxylic acid complex. The solution of zirconium-alkanolamine-hydroxycarboxylic acid complex, the base gel, or both further comprise a pH buffer.

The base gel is contacted with the solution of zirconium-alkanolamine-hydroxycarboxylic acid complex to form the cross-linked gel. The cross-linked gel is then introduced into the formation at a flow rate and pressure sufficient to create, reopen, and/or extend a fracture in the formation.

Alternatively, the subterranean formation may be penetrated by a wellbore, such that contacting the solution of zirconium-alkanolamine-hydroxycarboxylic acid complex with the base gel occurs in the wellbore and the cross-linked gel is introduced into the formation from the wellbore. This method of hydraulically fracturing a subterranean formation penetrated by a wellbore comprises (a) preparing a base gel by mixing a cross-linkable organic polymer with an aqueous liquid; (b) introducing the base gel into the wellbore; (c) simultaneously with or sequentially after introducing the base gel into the wellbore, introducing a solution of a zirconium-alkanolamine-hydroxycarboxylic acid complex, prepared as described previously; (d) permitting the base gel and the solution of zirconium complex to react to form a cross-linked aqueous gel; and (e) introducing the cross-linked gel into the formation from the wellbore at a flow rate and pressure sufficient to create, reopen, and/or extend a fracture in the formation. A pH buffer is independently admixed with the base gel, the solution of zirconium complex or both prior to introducing the base gel and the zirconium-alkanolamine-hydroxycarboxylic acid complex solution into the wellbore.

Upon creation of a fracture or fractures, the method may further comprise introducing a cross-linking composition comprising the solution of zirconium-alkanolamine-hydroxycarboxylic acid complex, a cross-linkable organic polymer and proppant into the fracture or fractures. This second introduction of a solution of zirconium-alkanolamine-hydroxycarboxylic acid complex is preferably performed in the event the cross-linking composition used to create the fracture or fractures did not comprise proppant.

Another use for the solution of zirconium-alkanolamine-hydroxycarboxylic acid complex of the present invention relates to a method for selectively plugging permeable zones and leaks in subterranean formations which comprises introducing into the permeable zone or the site of the subterranean leak, a cross-linking composition comprising an aqueous liquid; a pH buffer; a cross-linkable organic polymer; and a solution of a zirconium-alkanolamine-hydroxycarboxylic acid complex, prepared as described previously. The pH buffer may be admixed with the solution of zirconium complex prior to introducing the cross-linking composition into the permeable zone or site of the leak.

In a first embodiment of the method for plugging a permeable zone or a leak in a subterranean formation, the aqueous liquid, pH buffer, cross-linkable organic polymer and the solution of zirconium-alkanolamine-hydroxycarboxylic acid complex are contacted prior to their introduction into the subterranean formation, such that the polymer and zirconium complex react to form a cross-linked aqueous gel, which gel is then introduced into the formation.

In an alternative embodiment of the method for plugging a permeable zone or a leak in a subterranean formation, the solution of zirconium-alkanolamine-hydroxycarboxylic acid complex and the cross-linkable organic polymer are introduced separately, either simultaneously or sequentially, into the permeable zone or the site of the subterranean leak such that cross-linking occurs within the subterranean formation. This method comprises preparing a base gel by mixing a cross-linkable organic polymer with an aqueous liquid; introducing the base gel into the into the permeable zone or the site of the subterranean leak, simultaneously with or sequentially after, introducing the base gel into the into the permeable zone or the site of the subterranean leak, introducing the solution of zirconium-alkanolamine-hydroxycarboxylic acid complex into the into the permeable zone or the site of the subterranean leak; permitting the base gel and the cross-linking agent to react to form a cross-linked aqueous gel to plug the zone and/or leak. The solution of zirconium-alkanolamine-hydroxycarboxylic acid complex, the base gel, or both further comprise a pH buffer.

The relative amounts of cross-linkable organic polymer and the zirconium-alkanolamine-hydroxycarboxylic acid complex may vary. One uses small but effective amounts which for both will vary with the conditions, e.g., the type of subterranean formation, the depth at which the method (e.g., fluid fracturing, permeable zone plugging or leak plugging) is to be performed, temperature, pH, etc. Generally one uses as small an amount of each component as will provide the viscosity level necessary to effect the desired result, i.e., fracturing of the subterranean formation, or plugging permeable zones or leaks to the extent necessary to promote adequate recovery of oil or gas from the formation.

For example, satisfactory gels can generally be made for fluid fracturing by using the cross-linkable organic polymer in amounts up to about 1.2 weight % and the cross-linking composition in amounts up to about 0.50 weight % of the zirconium complex, with percentages being based on the total weight of the base gel. Preferably, from about 0.25 to about 0.75 weight % of the cross-linkable organic polymer is used and from about 0.05 to about 0.25 weight % of the zirconium complex is used.

In a method for plugging permeable zones or leaks, generally about 0.25 to 1.2 weight % of a cross-linkable organic polymer is used, preferably 0.40 to 0.75 weight %, based on the total weight of the base gel. Generally about 0.01 to 0.50 weight % of the zirconium complex is used, preferably 0.05 to 0.25 weight %, based on the total weight.

The amount of zirconium complex used to cross-link the organic polymer is that which provides a zirconium ion concentration in a range from about 0.0005 weight % to about 0.1 weight %, based on the total weight of the base gel. The preferred concentration of zirconium ion is in the range of from about 0.001-0.05 weight %, based on the total weight.

Typically the solution of zirconium complex of this invention can be used at a pH of from about 3 to 11. For low temperature applications (150-250° F., 66-121° C.), carbon dioxide-based energized fluids may be used. In this case, a pH for the cross-linking composition of about 3 to about 6 is preferred. For moderate or high temperature applications (275-400° F., 121-204° C.), a pH of about 9 to about 11 is preferred. Advantageously, the solution of zirconium complex of this invention is used at a temperature of 275-325° F. (135-163° C.). For successful completion of the fracturing operation, whether hydraulic fracturing or plugging a permeable zone, the cross-linking composition should provide a viscosity of at least 200 Cp, preferably at least 300 Cp, 90 minutes after introducing the cross-linking composition into the subterranean formation or permeable zone or site of a subterranean leak.

EXAMPLES

The preparation of the compositions in the Comparative Examples and in the Examples were each carried out in closed vessels containing an agitator, thermometer, condenser, nitrogen inlet and dropping funnel. Unless specified otherwise, percentages are given by weight. Temperatures are given in degrees Celsius. The cross-linking properties of the compositions of this invention are given in the Comparative Examples and in the Examples as a function of the viscosity of carboxymethylhydroxypropylguar cross-linked with the zirconate of this invention.

Preparation of Base Gel

A Waring blender jar was filled with 1 liter of distilled water. To this was added 2 g of a 50% aqueous solution of tetramethylammonium chloride clay stabilizer. Agitation was started and 3.6 g of carboxymethylhydroxypropylguar (CM-HPG) was sprinkled into the vortex of the agitating solution. The pH of the resultant slurry was adjusted to 6 with sodium diacetate and agitation continued for 30 minutes. The pH was then adjusted to 10.3 with 10% sodium hydroxide solution. Agitation was stopped and the gel was allowed to stand for 30 minutes or more before use.

Viscosity Measurement of Zirconate Cross-linked Base Gel

To 250 ml of a vigorously agitated sample of base gel in a Waring blender jar, was added 0.00032 moles of zirconium (0.2-1.0 ml dependent on percent zirconium of cross-linker solution—hereinafter referred to as the Standard Loading Density), for each Comparative Example A-E and each Example 1-4. Agitation was continued for about 15-180 seconds. A 25 ml sample of the cross-linker containing gel was placed in the cup of the FANN 50 Viscometer with an R-1, B-3 configuration and viscosity was measured at 250° F. (121° C.) and/or 275° F. (135° C.) and 122 rpm at 100 reciprocal seconds of shear.

Comparative Example A

Triethanolamine (135.2 g) was added to 100 g of tetra-n-propyl zirconate solution (TYZOR NPZ organic zirconate, available from E.I. du Pont de Nemours and Company, Wilmington, Del.). The reaction mixture was heated to 60° C. and held at this temperature for 4 hours. Upon completion of the reaction, the resultant solution of tetra(triethanolamine) zirconate was concentrated on a rotary evaporator under reduced pressure to yield 155 g of a viscous yellow oil, which contained 13.2% Zr.

Comparative Example B

Hydroxyethyl tris-2-hydroxypropyl ethylenediamine (146 g) was added to 220.3 g of tetra-n-propyl zirconate. The reaction mixture was heated to 60° C. and held at this temperature for 4 hours to give 346 g of a pale yellow liquid containing 12.4% Zr.

Comparative Example C

A 500-ml flask, equipped with a thermocouple, dropping funnel, N2 bleed and condenser was charged with 59.8 g of 85% lactic acid. Agitation was started and 61.6 g of triethanolamine and 50 g of water were added. The solution was cooled to 15° C. and then 122.5 g of 30% zirconium oxychloride solution were added. The pH was adjusted to 8.0 using 21.7 g of 28% ammonium hydroxide solution. The solution was diluted with 180 g of water to give 495 g of a water white solution containing 3.8% of Zr.

Comparative Example D

A 500-ml flask, equipped with a thermocouple, dropping funnel, N2 bleed and condenser was charged with 76.7 g of 85% lactic acid. Agitation was started and 66.7 g of di-isopropanolamine and 50 g of water were added. The solution was cooled to 15° C. and then 148.5 g of 30% zirconium oxychloride solution were added. The pH was adjusted to 9.0 using 25.7 g of 28% ammonium hydroxide solution. The solution was diluted with water to 600 g to give a water white solution containing 3.8% of Zr.

Comparative Example E

A 500-ml flask, equipped with a thermocouple, dropping funnel, N2 bleed and condenser was charged with 93.9 g of 85% lactic acid. Agitation was started and 222 g of water were added. The solution was heated to 90° C. and then 60 g of zirconium carbonate were added. The solution was held at 90° C. for 2 hours and then 93.5 g of triethanolamine were added dropwise. The solution was then held for another 30 minutes at 90° C. and then cooled to give a water white solution containing 3.8% of Zr.

Example 1

A 500-ml flask, equipped with a thermocouple, dropping funnel, N2 bleed and condenser was charged with 100 g of TYZOR NPZ organic zirconate. Agitation was started and 66.7 g of triethanolamine were added. The solution was heated to 60° C. and held at this temperature for 2 hours. Then, 69.6 g of 85% lactic acid were added. The solution was heated at 60° C. for an additional 2 hours to give 236 g of an orange liquid containing 8.8% of Zr.

Example 2

A 500-ml flask, equipped with a thermocouple, dropping funnel, N2 bleed and condenser was charged with 100 g of TYZOR NPZ organic zirconate. Agitation was started and 133.5 g of triethanolamine were added. The solution was heated to 60° C. and held at this temperature for 2 hours. Then, 46.5 g of 85% lactic acid were added. The solution was heated at 60° C. for an additional 2 hours to give 279 g of an orange liquid containing 7.4% of Zr.

Example 3

A 500-ml flask, equipped with a thermocouple, dropping funnel, N2 bleed and condenser was charged with 100 g of TYZOR NPZ organic zirconate. Agitation was started and 133.5 g of triethanolamine were added. The solution was heated to 60° C. and held at this temperature for 2 hours. Then, 69.6 g of 85% lactic acid were added. The solution was heated at 60° C. for an additional 2 hours to give 304 g of an orange liquid containing 6.8% of Zr.

Example 4

A 500-ml flask, equipped with a thermocouple, dropping funnel, N2 bleed and condenser was charged with 100 g of TYZOR NPZ organic zirconate. Agitation was started and 130 g of tri-isopropanolamine were added. The solution was heated to 60° C. and held at this temperature for 2 hours. Then, 69.6 g of 85% lactic acid were added. The solution was heated at 60° C. for an additional 2 hours to give 299 g of an orange liquid containing 6.9% of Zr.

The Table shows the performance of a 30 lb/1000 gallon (3600 g/1000 liters) CMHPG gel cross-linked with both products of Comparative Examples and those of the Examples of the invention. In this Table, Temp. refers to temperature in both degrees Fahrenheit (° F.) and degrees Celsius (° C.); % Zr refers to percent of zirconium in the solution of the zirconium complex, Zr solution, ml refers to the milliliters of cross-linker solution injected in each test. Zr compound provides the source of zirconium compound used to prepare each Comparative Example and Example, wherein NPZ refers to TYZOR NPZ organic zirconate; ZrOCl2 refers to zirconium oxychloride; and Zr carbonate refers to zirconium carbonate, 40% active as $ZrO_2$. Under the Alkanolamine column, TEA refers to triethanolamine; L-699 refers to hydroxyethyltrishydroxyisopropyl-ethylenediamine; DIPA refers to diisopropanolamine; and TIPA refers to triisopropanolamine. Under the hydroxycarboxylic acid column, LA refers to lactic acid. The values in parentheses, for the alkanol amine and hydroxycarboxylic acid columns, refer to molar ratio of the respective component relative to zirconium. Mole ratio of all Comparative Examples and Examples of the invention for zirconium is 1, by definition.

TABLE

| Example No. | Temp., °F. (°C.) | % Zr | Zr solution, ml | Zr compound | alkanol amines (moles) | hydroxy carboxylic acid (moles) | Fann Time Max, min. | Cp @ Max Tmac | Cp @ 90 min |
|---|---|---|---|---|---|---|---|---|---|
| Comp. Ex. A-1 | 250 (121) | 13.2 | 0.18 | NPZ | TEA (4) |  | 7 | 1180 | 795 |
| Comp. Ex. A-2 | 275 (135) | 13.2 | 0.18 | NPZ | TEA (4) |  | 1.5 | 1125 | 660 |
| Comp. Ex. B-1 | 250 (121) | 12.4 | 0.27 | NPZ | L-699 (1) |  | 20 | 306 | 226 |
| Comp. Ex. B-2 | 275 (135) | 12.4 | 0.27 | NPZ | L-699 (1) |  | 12 | 300 | 225 |
| Comp. Ex. C-1 | 250 (121) | 3.8 | 0.78 | ZrOCl2 | TEA (2) | LA (3) | 5.5 | 1220 | 300 |
| Comp. Ex. C-2 | 275 (135) | 3.8 | 0.78 | ZrOCl2 | TEA (2) | LA (3) | 6.5 | 490 | 75 |
| Comp. Ex. D-1 | 250 (121) | 3.8 | 0.74 | ZrOCl2 | DIPA (2) | LA (3) | 6.0 | 830 | 310 |
| Comp. Ex. D-2 | 275 (135) | 3.8 | 0.74 | ZrOCl2 | DIPA (2) | LA (3) | 5 | 400 | 175 |
| Comp. E | 275 (135) | 3.8 | 0.78 | Zr carbonate | TEA (3.24) | LA (4.6) | 5.5 | 1080 | 10 |
| Ex. 1-1 | 250 (121) | 8.8 | 0.34 | NPZ | TEA (2) | LA (3) | 6 | 1162 | 502 |
| Ex. 1-2 | 275 (135) | 8.8 | 0.34 | NPZ | TEA (2) | LA (3) | 4.5 | 1150 | 465 |
| Ex. 2-1 | 250 (121) | 7.4 | 0.40 | NPZ | TEA (4) | LA (2) | 7.5 | 580 | 395 |
| Ex. 2-2 | 275 (135) | 7.4 | 0.40 | NPZ | TEA (4) | LA (2) | 5 | 700 | 312 |
| Ex. 3-1 | 250 (121) | 6.8 | 0.44 | NPZ | TEA (4) | LA (3) | 8 | 905 | 390 |
| Ex. 3-2 | 275 (135) | 6.8 | 0.44 | NPZ | TEA (4) | LA (3) | 6 | 870 | 360 |
| Ex. 4-1 | 250 (121) | 6.9 | 0.43 | NPZ | TIPA (3) | LA (3) | 5.5 | 770 | 400 |
| Ex. 4-2 | 275 (135) | 6.9 | 0.40 | NPZ | TIPA (3) | LA (3) | 4.5 | 720 | 370 |

"Fann Time Max, min." means the time in minutes it takes to reach maximum viscosity. The viscosity at this maximum time is labeled "Cp @ Max." to indicate viscosity in centipoise (Cp). The viscosity after 90 minutes at the test temperature is labeled "Cp @ 90 min."

As can be seen from the Table, the zirconium—triethanolamine cross-linking composition in Comp. Example A showed the desired cross-linking rate, as measured by time to reach maximum viscosity, and generated excellent viscosity at 250° F. (121° C.). However at 275° F. (135° C.), the rate of cross-linking was much too fast at 1.5 minutes. In the field, at this rate of cross-linking, shear degradation and loss of viscosity of the cross-linked gel would be expected, prior to reaching the zone to be fractured or plugged in the formation.

The composition prepared in Comparative Example B cross-linked much too slowly at both 250° F. (121° C.) and 275° F. (135° C.). Sand would be expected to precipitate out of the suspension before adequate viscosity developed, causing a "sand out" when this composition was used in an actual oil field in a fracturing fluid/cross-linking composition.

The composition prepared in Comparative Example E, based on Example 1 of U.S. Pat. No. 5,798,320, cross-linked at the desired rate; however gave a gel which was highly shear-unstable and rapidly lost viscosity at a temperature of 275° F. (135° C.).

The solvent-based cross-linkers of the invention as prepared according to Examples 1-4, and aqueous-based zirconium-triethanolamine-lactic acid complexes, as prepared according to Comparative Examples C and D cross-linked in the desired 3-8 minute range at temperatures of 250° F. (121° C.) and 275° F. (135° C.). However the solvent-based zirconate complexes of Examples 1-4 had generally higher viscosities than the aqueous-based zirconates of Comparative Examples C and D at 250° F. (121° C.). More significantly, the solvent-based zirconate complexes of Examples 1-4 retained more viscosity at 275° F. (135° C.), which allows them to be used over a broader temperature range. The aqueous-based zirconates of Comparative Examples C and D maintained insufficient viscosity at 275° F. (135° C.), for successful completion of the fracturing operation.

What is claimed is:

1. A process for preparing a zirconium complex suitable for cross-linking a fracturing fluid which comprises: (a) contacting an alcohol solution of a zirconium complex with an alkanolamine at a mole ratio of 2 to 4 moles of alkanolamine per mole of zirconium to form a mixture which is a solvent-based alkanolamine complex of zirconium;

(b) contacting the mixture with an α-hydroxycarboxylic acid at a mole ratio of 2 to 4 moles of hydroxycarboxylic acid per mole of zirconium for a period of time sufficient to stabilize the resulting solution of zirconium-alkanolamine-hydroxycarboxylic acid complex.

2. The process of claim 1 wherein the zirconium complex is a tetraalkyl zirconate selected from the group consisting of tetra-isopropyl zirconate, tetra-n-propyl zirconate, and tetra-n-butyl zirconate.

3. The process of claim 2 wherein the alkanolamine is selected from the group consisting of triethanolamine, tri-n-propanolamine, tri-isopropanolamine, diisopropanolamine, and mixtures thereof.

4. The process of claim 3 wherein the a-hydroxycarboxylic acid is selected from the group consisting of lactic acid, glycolic acid, malic acid, citric acid, and mixtures thereof.

5. The process of claim 4 wherein the alcohol solvent in step (a) is an aliphatic alcohol having 1 to 6 carbon atoms.

6. The process of claim 5 wherein the alcohol is methanol, isopropanol, or n-propanol and the mole ratio of aliphatic alcohol to zirconium is at least 4 to 1 moles of alcohol per mole of zirconium.

7. The process of claim 5 wherein the alkanolamine is triethanolamine and the α-hydroxycarboxylic acid is lactic acid.

8. A cross-linking composition which comprises an aqueous liquid; a pH buffer; a cross-linkable organic polymer; and a solution of zirconium-alkanolamine-hydroxycarboxylic acid complex prepared by a process which comprises: (a) contacting an alcohol solution of a zirconium complex with an alkanolamine at a mole ratio of 2 to 4 moles of alkanolamine per mole of zirconium to form a mixture which is a solvent-based alkanolamine complex of zirconium; (b) contacting the mixture with an α-hydroxycarboxylic acid at a mole ratio of 2 to 4 moles of hydroxycarboxylic acid per mole of zirconium for a period of time sufficient to stabilize the resulting solution of zirconium-alkanolamine-hydroxycarboxylic acid complex.

9. The composition of claim 8 wherein the organic polymer is a solvatable polysaccharide and is selected from the group consisting of gums, gum derivatives and cellulose derivatives.

10. The composition of claim 9 wherein the organic polymer is hydroxyethylguar, hydroxypropylguar, carboxyethylhydroxyethylguar, carboxymethylhydroxypropylguar, or carboxymethyl guar.

11. The composition of claim 8 wherein the aqueous liquid is selected from the group consisting of water, aqueous alcohol, and aqueous solution of a clay stabilizer.

12. The composition of claim 8 wherein the aqueous liquid is water, aqueous methanol, aqueous ethanol, an aqueous solution of potassium chloride, an aqueous solution of tetramethylammonium chloride, or a combination of two or more thereof.

13. A method for hydraulically fracturing a subterranean formation, which comprises introducing into the formation at a flow rate and pressure sufficient to create, reopen, and/or extend one or more fractures in the formation, a cross-linking composition comprising an aqueous liquid; a pH buffer; a cross-linkable organic polymer, and a solution of a zirconium-alkanolamine-hydroxycarboxylic acid complex wherein the solution is prepared by a process comprising: (a) contacting an alcohol solution of a zirconium complex with an alkanolamine at a mole ratio of 2 to 4 moles of alkanolamine per mole of zirconium to form a mixture which is a solvent-based alkanolamine complex of zirconium; (b) contacting the mixture with an α-hydroxycarboxylic acid at a mole ratio of 2 to 4 moles of hydroxycarboxylic acid per mole of zirconium for a period of time sufficient to stabilize the resulting solution of zirconium-alkanolamine-hydroxycarboxylic acid complex.

14. The method of claim 13 wherein the temperature in the formation is 275-325° F. (135-163° C.).

15. The method of claim 14 wherein the solution of zirconium-alkanolamine-hydroxycarboxylic acid complex and the cross-linkable polymer are contacted prior to their introduction into the formation.

16. The method of claim 15 wherein a base gel is prepared by mixing the cross-linkable organic polymer with the aqueous liquid; the base gel is contacted with the solution of zirconium-alkanolamine-hydroxycarboxylic acid complex to form a cross-linked gel; the cross-linked gel is then introduced into the formation at a flow rate and pressure sufficient to create, reopen, and/or extend a fracture in the formation wherein the solution of zirconium-alkanolamine-hydroxycarboxylic acid complex, the base gel, or both further comprise a pH buffer.

17. The method of claim 14 wherein the subterranean formation is penetrated by a wellbore;
a base gel is prepared by mixing the cross-linkable organic polymer with the aqueous liquid;
the solution of zirconium-alkanolamine-hydroxycarboxylic acid complex, the base gel, or both further comprise a pH buffer;
the solution of zirconium-alkanolamine-hydroxycarboxylic acid complex is contacted with the base gel in the wellbore to produce a cross-linked gel, and
the cross-linked gel is introduced into the formation from the wellbore.

18. The method of claim 14 further comprising introducing a cross-linking composition comprising the solution of zirconium-alkanolamine-hydroxycarboxylic acid complex, a cross-linkable organic polymer and proppant into the fracture or fractures.

19. A method for selectively plugging permeable zones and leaks in subterranean formations which comprises introducing into the permeable zone or the site of the subterranean leak, a cross-linking composition comprising an aqueous liquid; a pH buffer, a cross-linkable organic polymer; and a solution of a zirconium-alkanolamine-hydroxycarboxylic acid complex comprising an aqueous liquid; a pH buffer; a cross-linkable organic polymer, and a solution of a zirconium-alkanolamine-hydroxycarboxylic acid complex wherein the solution is prepared by a process comprising: (a) contacting an alcohol solution of a zirconium complex with an alkanolamine at a mole ratio of 2 to 4 moles of alkanolamine per mole of zirconium to form a mixture which is a solvent-based alkanolamine complex of zirconium; (b) contacting the mixture with an α-hydroxycarboxylic acid at a mole ratio of 2 to 4 moles of hydroxycarboxylic acid per mole of zirconium for a period of time sufficient to stabilize the resulting solution of zirconium-alkanolamine-hydroxycarboxylic acid complex.

20. The method of claim 19 wherein the temperature in the formation is 275-325° F. (135-163° C.).

21. The method of claim 20 wherein the aqueous liquid, pH buffer, cross-linkable organic polymer and the solution of zirconium-alkanolamine-hydroxycarboxylic acid complex are contacted prior to their introduction into the permeable zone or the site of the subterranean leak.

22. The method of claim 20 wherein the solution of zirconium-alkanolamine-hydroxycarboxylic acid complex and the cross-linkable organic polymer are introduced separately and sequentially into the permeable zone or the site of the subterranean leak.

23. The method of claim 20 wherein the solution of zirconium-alkanolamine-hydroxycarboxylic acid complex and the cross-linkable organic polymer are introduced separately and simultaneously into the permeable zone or the site of the subterranean leak.

\* \* \* \* \*